(12) United States Patent
Chauhan et al.

(10) Patent No.: US 9,107,929 B2
(45) Date of Patent: Aug. 18, 2015

(54) STABLE PARENTERAL FORMULATIONS OF TIGECYCLINE

(75) Inventors: Bhaskar Chauhan, Chandausi (IN); Vinod Kumar Arora, Gurgaon (IN); Jyoti Srivastava, Gurgaon (IN)

(73) Assignee: RANBAXY LABORATORIES LIMITED, New Delhi (IN)

( * ) Notice: Subject to any disclaimer, the term of this patent is extended or adjusted under 35 U.S.C. 154(b) by 867 days.

(21) Appl. No.: 12/434,499

(22) Filed: May 1, 2009

(65) Prior Publication Data

US 2009/0275660 A1 Nov. 5, 2009

(30) Foreign Application Priority Data

May 1, 2008 (IN) ............................ 1110/DEL/2008

(51) Int. Cl.
| | | |
|---|---|---|
| *A01N 43/00* | (2006.01) | |
| *A61K 31/33* | (2006.01) | |
| *A61K 31/65* | (2006.01) | |
| *A61K 9/00* | (2006.01) | |
| *A61K 9/08* | (2006.01) | |
| *A61K 9/19* | (2006.01) | |

(52) U.S. Cl.
CPC ............... *A61K 31/65* (2013.01); *A61K 9/0019* (2013.01); *A61K 9/08* (2013.01); *A61K 9/19* (2013.01)

(58) Field of Classification Search
None
See application file for complete search history.

(56) References Cited

U.S. PATENT DOCUMENTS

| | | | |
|---|---|---|---|
| 5,494,903 A | 2/1996 | Hlavka et al. | .......... A61K 31/65 |
| RE40,086 E | 2/2008 | Hlavka et al. | .......... A61K 31/65 |
| 2002/0098208 A1* | 7/2002 | Wooley et al. | ................. 424/400 |
| 2004/0208842 A1* | 10/2004 | Ritchie et al. | ............. 424/70.21 |

FOREIGN PATENT DOCUMENTS

| | | | | |
|---|---|---|---|---|
| CN | 101152152 A | * | 4/2008 | |
| WO | WO 2006/099258 | | 9/2006 | ............... A61K 9/19 |
| WO | WO 2006/138641 | | 12/2006 | ............... A61K 9/19 |
| WO | WO 2007/075794 | | 7/2007 | ............... A61K 9/16 |

OTHER PUBLICATIONS

CAPlus; Assension No. 2008:428891; Document No. 148:434151; 2008.*
Zhang et al.; CN 101152152 A; Apr. 2, 2008; Machine Translation.*
Hunter et al., "Safety to Human Skin of Cocamidopropyl Betaine: A Mild Surfactant for Personal-Care Products," Journal of Surfactants and Detergents, vol. 1, No. 2 (Apr. 1998).*

* cited by examiner

*Primary Examiner* — Craig Ricci
*Assistant Examiner* — Jared D Barsky

(57) ABSTRACT

The invention relates to stable parenteral formulations of tigecycline and process of preparation thereof, wherein the formulation comprises an edetate, a pH modifying agent or an antioxidant, such that the formulation remains stable for at least 45 hours.

10 Claims, No Drawings

STABLE PARENTERAL FORMULATIONS OF TIGECYCLINE

TECHNICAL FIELD OF THE INVENTION

The present invention relates to stable parenteral formulations of tigecycline and process of preparation thereof.

BACKGROUND OF THE INVENTION

Tigecycline is the first antibiotic belonging to the glycylcycline class, and the first new tetracycline analogue launched in over 30 years. It acts by binding to the bacterial 30S ribosome and thereby blocking the entry of amino-acyl t-RNA molecules into the A site of ribosome. This ultimately prevents protein synthesis by halting the incorporation of amino acids into peptide chains and thus limits bacterial growth. Chemically, it is known as (4S,4aS,5aR,12aS)-9-[2-(tert-butylamino)acetamido]-4,7-bis(dimethylamino)-1,4,4a,5,5a,6,11,12a-octahydro-3,10,12,12a-tetrahydroxy-1,11-dioxo-2-naphthacene carboxamide and structurally represented as follows:

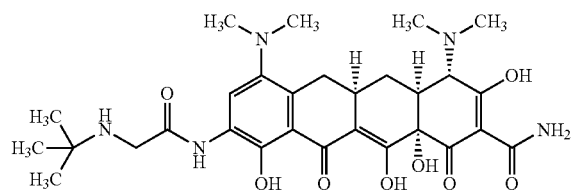 [SMILES: CN(C)c1cc(NC(=O)CNC(C)(C)C)c(O)c2c1C[C@H]1C[C@H]3[C@H](N(C)C)C(O)=C(C(N)=O)C(=O)[C@@]3(O)C(O)=C1C2=O]

The U.S. Pat. No. 5,494,903 discloses tigecycline and the pharmaceutically acceptable organic and inorganic salts or metal complexes. U.S. Pat. No. RE 40,086 describes the use of tigecycline in treating and controlling bacterial infections in warm blooded animals. Owing to its poor oral bioavailability, it is advantageous to administer tigecycline parenterally. In India, it is commercialized by Wyeth Limited in strengths of 50 mg/vial as an orange lyophilized powder or cake for intravenous administration under the proprietary name TYGACIL® (tigecycline). It is indicated for treatment of the following infections in adults: (a) complicated skin and skin structure infections, including those with methicillin-resistant *staphylococcus aureus* (MRSA) and (b) complicated intra-abdominal infections. The standard dosage regimen for tigecycline is an initial dose of 100 mg, followed by 50 mg every 12 hours.

Several documents disclose formulations containing tigecycline and process of formulating thereof. For example, WO 2006/138641 refers to a process for manufacturing a reconstitutable lyophilized composition of tigecycline, wherein the process comprises of admixing tigecycline with water for injection (while reducing the oxygen level and maintaining the reduced oxygen level in the water for injection); lyophilizing the composition containing tigecycline and water for injection and sealing the vials containing lyophilized composition under nitrogen. Another PCT application, WO 2007/075794 describes an oral composition containing tigecycline with at least one enteric coating. It further discloses that calcium binds to tigecycline, resulting in the reduction of its water solubility which in turn may lead to a 30% to 40% loss of tigecycline due to precipitation of the calcium complex at pH 7.4. Thus, calcium binding and subsequent precipitation of the calcium/tigecycline salt may be at least partially responsible for low oral bioavailability. Hence, the disclosed oral compositions may further contain a chelating agent, like EDTA which would help in solving the problem of poor oral bioavailability of tigecycline by chelating any calcium present.

Per the TYGACIL® (tigecycline) Prescribing Information (Wyeth, India), tigecycline lyophilized powder should be reconstituted with 5.3 mL of 0.9% sodium chloride injection, USP, or 5% dextrose injection, USP, to achieve a concentration of 10 mg/mL of tigecycline. The Prescribing Information notes that the reconstituted solution should be discarded if it is not yellow to orange in color. At the concentration of 10 mg/mL, tigecycline degrades in solution and therefore, it becomes essential that these reconstituted solutions are immediately diluted to about 1 mg/mL with saline or other pharmaceutically acceptable carriers into intravenous bags for administration to patients. However, once reconstituted it may be stored at room temperature for up to 6 hours, or refrigerated at 2° C. to 8° C. for up to 24 hours. Hence, the individuals concerned with the reconstitution and administration of tigecycline injection, like doctors, attendants, other hospital staff, need administer the reconstituted formulation of tigecycline immediately to the person in need of the medicament. This makes the whole process of administering tigecycline to a person in need of it, prone to mistakes and extremely inconvenient and patient unfriendly.

The above-discussed oxidative degradations of tigecycline are decreased to a great extent by reducing the pH of tigecycline formulations. This, however lowering the pH affects the stability as it results in epimerization, which is an inherent property of tetracyclines and which is severe in case of tigecycline. Thus degradation by oxidation and/or epimerization is a major drawback while administering tigecycline to a person in need of. The PCT application WO 2006/099258 addresses this problem, and describes a formulation of tigecycline comprising a carbohydrate and an acid or buffer, which does not require immediate use and also helps in providing stability from both oxidation and epimerization for a maximum of 24 hours of admixture/dilution with a suitable carrier. However, in the present case, it has been observed that formulating together tigecycline, an edetate, and a pH-modifying agent or an antioxidant gives a stable parenteral formulation which would provide stability from degradation by oxidation as well as epimerization at least for 45 hours.

SUMMARY OF THE INVENTION

In one general aspect, it relates to a stable parenteral formulation comprising (a). tigecycline; (b) an edetate; (c) a pH-modifying agent or an antioxidant; and (d) optionally, other pharmaceutically acceptable excipients.

In another general aspect, it relates to a stable parenteral formulation comprising (a) tigecycline; (b) an edetate; (c) a pH-modifying agent or an antioxidant; and (d) optionally, other pharmaceutically acceptable excipients, wherein the formulation does not degrade at least for 45 hours.

In another general aspect, it relates to a process of preparation of a stable parenteral formulation comprising (a) tigecycline; (b) an edetate; (c) a pH-modifying agent or an antioxidant; and (d) optionally, other pharmaceutically acceptable excipients, wherein process comprises
 i. dissolving tigecycline, edetate, pH modifying agent or an antioxidant and optionally other pharmaceutically acceptable excipients in a suitable solvent;
 ii. filtering the solution in step (i) under aseptic conditions and filling it in vials;
 iii. optionally lyophilizing the solution in step (ii); and
 iv. stoppering and sealing the solution in step (ii), or the lyophilizate in step (iii) under vacuum.

DETAILED DESCRIPTION OF THE INVENTION

The terms "stable parenteral formulation" encompasses sterile solutions, as well as sterile or lyophilized powders and cakes which may be reconstituted into solutions by admixing with pharmaceutically acceptable carriers, and wherein the formulation would achieve stability against degradation of tigecycline by epimerization and/or oxidation. Such formulations may be administered via intravenous route. In one embodiment, the term "stable parenteral formulation" refers to a formulation that remains stable from degradation at least for 45 hours.

The term "tigecycline" as described herein, means a therapeutically effective amount of tigecycline or pharmaceutically acceptable salts, enantiomers, solvates, hydrates, polymorphs, and complexes thereof.

The term "edetate" as referred to herein, includes ethylenediamine tetraacetic acid (EDTA) and derivatives thereof, for example, disodium edetate, trisodium edetate, tetrasodium edetate, disodium calcium edentate, and the like.

The pH-modifying agents that may be used includes acids and or/buffers that is required to prevent degradation from oxidation and/or epimerization of the stable parenteral formulation as described herein, and that which helps in modifying the pH of the said formulation from about 3.0 to about 5.0. Any acid/buffer which does not adversely affect the effectiveness of the drug formulations may be employed. Acids may be exemplified as hydrochloric, succinic, L-(+)-lactic or L-tartaric acid, and the like. Buffers may be selected from citrate, acetate or phosphate buffer and the like. In one particular embodiment, 1.0N hydrochloric acid/1.0N sodium hydroxide is used.

Examples of antioxidants include without limitation, sodium metabisulphite, acetone sodium metabisulphite, sodium formaldehyde sulfoxylate, citric acid, d,l-α-tocopherol, butylated hydroxy anisole, butylated hydroxy toluene, monothioglycerol, ascorbic acid, propyl gallate, or the like.

Other pharmaceutically acceptable excipients may also be employed in the stable parenteral formulations as described herein, and may be exemplified as diluents, like sugars (e.g., lactose), sugar alcohols or other complex carbohydrates (e.g., cyclodextrins), and the like.

Further, preservatives, surfactants, antimicrobial agents, tonicity modifiers, and the like, which are conventionally used for parenteral solutions, and which are compatible with tigecycline and/or edetate and which will not interfere with the manufacture, storage or use of the final formulation may be incorporated in the stable parenteral formulations referred to herein.

The pharmaceutically acceptable carriers that may be employed for admixing with the sterile or lyophilized powders or cakes include vehicles customarily used for administering parenteral solutions such as water, sodium chloride solution, Ringer's solution, dextrose solution, dextrose and sodium chloride solution, lactated Ringer's solution, and the like.

The stable parenteral formulations may be stored in sealed containers, e.g., glass vials, having vacuum headspaces. The active ingredient, i.e., tigecycline is mixed with an edetate and dissolved in a suitable solvent, which for example may be sterile, pyrogen-free water for injection. The said water for injection may be purged with an inert gas through the said solution, to remove gaseous impurities and reduce the amount of residual oxygen therein. Further, the temperature may be maintained below 10° C., preferably below 8° C. In one embodiment, the purging gas is nitrogen.

Lyophilization of the solutions may be done by any available conventional pharmaceutical method.

In one embodiment, the stable parenteral formulation comprises (a) tigecycline; (b) disodium edetate; and (c) hydrochloric acid.

In another embodiment, the stable parenteral formulation comprises (a) tigecycline; (b) disodium edetate; and (c) sodium metabisulphite.

In another embodiment, the stable parenteral formulation comprises (a) tigecycline; (b) disodium edetate; (c) sodium metabisulphite; and (d) lactose.

In another embodiment, the stable parenteral formulation may be prepared by the process, wherein the process comprises of i. dissolving tigecycline, disodium edetate in sterile, pyrogen-free water for injection which is maintained at temperature below 10° C. and purged with nitrogen gas;

ii. adjusting the pH of the solution in step (i) using 0.1N hydrochloric acid/0.1N sodium hydroxide;

iii. filtering the solution in step (ii) under aseptic conditions, filling it in vials and partially stoppering the said vials;

iv. lyophilizing solution in vials in step (iii); and v. stoppering and sealing the lyophilizate in step (iv) under vacuum.

In another embodiment, the stable parenteral formulation may be prepared by the process, wherein the process comprises of:

i. dissolving tigecycline, disodium edetate in sterile, pyrogen-free water for injection which is maintained at temperature below 10° C. and purged with nitrogen gas;

ii. adding sodium metabisulphite in the solution of step (i);

iii. filtering the solution in step ii under aseptic conditions, filling it in vials and partially stoppering the said vials;

iv. lyophilizing solution in vials in step (iii); and v. stoppering and sealing the lyophilizate in step (iv) under vacuum.

In another embodiment, the stable parenteral formulation may be prepared by the process, wherein the process comprises of:

i. dissolving tigecycline, disodium edetate in sterile, pyrogen-free water for injection which is maintained at temperature below 10° C. and purged with nitrogen gas;

ii. adding sodium metabisulphite and lactose in the solution of step (i);

iii. filtering the solution in step (ii) under aseptic conditions, filling it in vials and partially stoppering the vials;

iv. lyophilizing solution in vials in step (iii); and v. stoppering and sealing the lyophilizate in step (iv) under vacuum.

The stable parenteral formulations comprising (a) tigecycline; (b) an edetate; (c) a pH-modifying agent or an antioxidant; and (d) optionally, other pharmaceutically acceptable excipients, and process of preparation thereof described herein is further illustrated by the following examples, but, these should not be construed as limiting the scope of invention.

EXAMPLES

| SN | Ingredients | Quantity | | |
|---|---|---|---|---|
| | | Comparative Example | Example 1 | Example 2 |
| 1 | Tigecycline | 50.00 mg | 50.00 mg | 50.00 mg |
| 2 | Disodium edetate | — | 2.50 mg | 1.00 mg |
| 3 | 1.0N Hydrochloric acid | — | q.s | — |
| 4 | 1.0N Sodium hydroxide | — | q.s | — |
| 5 | Lactose monohydrate | — | — | 100.00 mg |
| 6 | Sodium metabisulphite | — | — | 0.05 mg |
| 7 | Water for injection | q.s. to 1.5 mL | q.s. to 1.5 mL | q.s. to 1.5 mL |
| | pH of the final solution prior to lyophilization: | 7.4 | 4.0-5.0 | 7.0-8.0 |

Procedure:

Comparative Example

Tigecycline was dissolved in water for injection (cooled to a temperature of 2 to 8° C.) under continuous stirring. The solution was filtered and filled into USP Type I glass vial (1.5 mL). The glass vials were partially stoppered and lyophilized. The lyophilized vials were finally stoppered and sealed under inert conditions.

Example 1

Disodium edetate was dissolved in water for injection (cooled to a temperature of 2 to 8° C. and oxygen content lowered by continuous purging of nitrogen gas). In the solution obtained, tigecycline was added under continuous stirring. The pH of this solution was adjusted to 4.0 to 5.0 with 1.0N hydrochloric acid/1.0N sodium hydroxide solution. The final solution was filtered and filled into USP Type I glass vials (1.5 mL). The glass vials were partially stoppered and lyophilized. The lyophilized vials were finally stoppered and sealed under vacuum.

Example 2

Disodium edetate was dissolved in water for injection (cooled to a temperature of 2 to 8° C. and oxygen content lowered by continuous purging of nitrogen gas). In the solution obtained, lactose monohydrate, sodium metabisulphite and tigecycline were added under continuous stirring. The final solution was filtered and filled into USP Type I glass vials (1.5 mL). The glass vials were partially stoppered and lyophilized. The lyophilized vials were finally stoppered and sealed under vacuum.

The lyophilized vials of Comparative Example, Examples 1 and 2 were stored at 80° C. for 3 days, at 60° C. for 15 days, and at accelerated stability conditions of 40° C. and 75% relative humidity for 30 days, 60 days and 90 days. Each of the stored vials were then reconstituted separately with (a) 5.3 mL 0.9% sodium chloride solution; and (b) 5.3 mL 5% dextrose solution and compared with the reconstituted solutions of the marketed TYGACIL® (tigecycline) lyophilized powder (Batch No. 30819) available from Wyeth Limited, India (manufactured in the UK) (a) 5.3 mL 0.9% sodium chloride solution; and (b) 5.3 mL 5% dextrose solution. The reconstituted solutions were stored at room temperature. The color of the reconstituted solutions was observed in daylight at 6 and 48 hour intervals, and the observation as recorded is given in Tables 1-5.

TABLE 1

The color of reconstituted formulations of TYGACIL ® (tigecycline) (Batch No. 30819) available from Wyeth (India), manufactured in the UK; and Comparative Example, Example 1 and Example 2 which were previously stored at 80° C. for 3 days, at different time intervals

| Storage Time of the Reconstituted Formulation at Room Temperature (Hr) | Color of the Reconstituted Formulations Prepared in (a) 5.3 mL 0.9% Sodium Chloride Solution; and (b) 5.3 mL 5% Dextrose Solution for | | | | | | | |
|---|---|---|---|---|---|---|---|---|
| | TYGACIL ® (tigecycline) (B. No 30819) Available from Wyeth (India); Manufactured in the UK | | Composition in Comparative Example, Previously Stored at 80° C. for 3 Days | | Composition in Example 1, Previously Stored at 80° C. for 3 Days | | Composition in Example 2, Previously Stored at 80° C. for 3 Days | |
| | 0.9% sodium chloride | 5% dextrose | 0.9% sodium chloride | 5% dextrose | 0.9% sodium chloride | 5% dextrose | 0.9% sodium chloride | 5% dextrose |
| 0 | Orange | Orange | Orange | Orange | Orange | Orange | Orange | Orange |
| 6 | Green | Green | Green | Green | Orange | Orange | Orange | Orange |
| 48 | Green | Green | Green | Green | Orange | Orange | Orange | Orange |

TABLE 2

The color of reconstituted formulations of TYGACIL ®
(tigecycline) (Batch. No. 30819) available
from Wyeth (India), manufactured in the UK; and Comparative Example, Example 1 and
Example 2 which were previously stored at 60° C. for 15 days at different time intervals Color of the Reconstituted Formulations Prepared in (a) 5.3 mL 0.9%
Sodium Chloride Solution; and (b) 5.3 mL 5% Dextrose Solution for

| Storage Time of the Reconstituted Formulation at Room Temperature (Hr) | TYGACIL ® (tigecycline) (B. No 30819) Available from Wyeth (India); Manufactured in the UK | | Composition in Comparative Example, Previously stored at 60° C. for 15 Days | | Composition in Example 1, Previously Stored at 60° C. for 15 Days | | Composition in Example 2, Previously Stored at 60° C. for 15 Days | |
|---|---|---|---|---|---|---|---|---|
| | 0.9% sodium chloride | 5% dextrose | 0.9% sodium chloride | 5% dextrose | 0.9% sodium chloride | 5% dextrose | 0.9% sodium chloride | 5% dextrose |
| 0 | Orange | Orange | Orange | Orange | Orange | Orange | Orange | Orange |
| 6 | Green | Green | Green | Green | Orange | Orange | Orange | Orange |
| 48 | Green | Green | Green | Green | Orange | Orange | Orange | Orange |

TABLE 3

The color of reconstituted formulations of TYGACIL ®
(tigecycline) (Batch No. 30819) available
from Wyeth (India), manufactured in the UK; and Comparative Example, Example 1 and
Example 2 which were previously stored at 40° C. and 75% relative humidity for
30 days at different time intervals Color of the Reconstituted Formulations Prepared in (a) 5.3 mL 0.9%
Sodium Chloride Solution; and (b) 5.3 mL 5% Dextrose Solution for

| Storage Time of the Reconstituted Formulation at Room Temperature (Hr) | TYGACIL ® (tigecycline) (B. No 30819) Available from Wyeth (India); Manufactured in the UK | | Composition in Comparative Example, Previously Stored at 40° C./75% RH for 30 Days | | Composition in Example 1, previously Stored at 40° C./75% RH for 30 Days | | Composition in Example 2, Previously Stored at 40° C./75% RH for 30 Days | |
|---|---|---|---|---|---|---|---|---|
| | 0.9% sodium chloride | 5% dextrose | 0.9% sodium chloride | 5% dextrose | 0.9% sodium chloride | 5% dextrose | 0.9% sodium chloride | 5% dextrose |
| 0 | Orange | Orange | Orange | Orange | Orange | Orange | Orange | Orange |
| 6 | Green | Green | Green | Green | Orange | Orange | Orange | Orange |
| 48 | Green | Green | Green | Green | Orange | Orange | Orange | Orange |

TABLE 4

The color of reconstituted formulations of TYGACIL ®
(tigecycline) (Batch No. 30819) available
from Wyeth (India), manufactured in the UK; and Comparative Example, Example 1 and
Example 2 which were previously stored at 40° C. and 75% relative humidity for
60 days at different time intervals Color of the Reconstituted Formulations Prepared in (a) 5.3 mL 0.9%
Sodium Chloride Solution; and (b) 5.3 mL 5% Dextrose Solution for

| Storage Time of the Reconstituted Formulation at Room Temperature (Hr) | TYGACIL ® (tigecycline) (Batch No. 30819) available from Wyeth (India); Manufactured at UK | | Composition in Comparative Example, previously stored at 40° C./75% RH for 60 Days | | Composition in Example 1, previously stored at 40° C./75% RH for 60 Days | | Composition in Example 2, previously stored at 40° C./75% RH for 60 Days | |
|---|---|---|---|---|---|---|---|---|
| | 0.9% sodium chloride | 5% dextrose | 0.9% sodium chloride | 5% dextrose | 0.9% sodium chloride | 5% dextrose | 0.9% sodium chloride | 5% dextrose |
| 0 | Orange | Orange | Orange | Orange | Orange | Orange | Orange | Orange |
| 6 | Green | Green | Green | Green | Orange | Orange | Orange | Orange |
| 48 | Green | Green | Green | Green | Orange | Orange | Orange | Orange |

TABLE 5

The color of reconstituted formulations of TYGACIL ®
(tigecycline) (B. No 30819) available from
Wyeth (India), manufactured in the UK; and Comparative Example, Example 1
and Example 2 which were previously stored at 40° C. and 75% relative humidity
for 90 days at different time intervals Color of the Reconstituted Formulations Prepared in (a) 5.3 mL 0.9%
Sodium Chloride Solution; and (b) 5.3 mL 5% Dextrose Solution for

| Storage Time of the Reconstituted Formulation at Room Temperature (Hr) | TYGACIL ® (tigecycline) (Batch No. 30819) available from Wyeth (India); Manufactured in the UK | | Composition in Comparative Example, previously stored at 40° C./75% RH for 90 Days | | Composition in Example 1, previously stored at 40° C./75% RH for 90 Days | | Composition in Example 2, previously stored at 40° C./75% RH for 90 Days | |
|---|---|---|---|---|---|---|---|---|
| | 0.9% sodium chloride | 5% dextrose | 0.9% sodium chloride | 5% dextrose | 0.9% sodium chloride | 5% dextrose | 0.9% sodium chloride | 5% dextrose |
| 0 | Orange | Orange | Orange | Orange | Orange | Orange | Orange | Orange |
| 6 | Green | Green | Green | Green | Orange | Orange | Orange | Orange |
| 48 | Green | Green | Green | Green | Orange | Orange | Orange | Orange |

Example 1 and TYGACIL® (tigecycline) [(Batch No. 30819) available from Wyeth, India; manufactured in the UK] vials were reconstituted separately with (a) 5.3 mL 0.9% sodium chloride solution; and (b) 5.3 mL 5% dextrose solution. From each vial 5 mL of the reconstituted solution were separately withdrawn and added to a 100 mL IV bag for infusion separately, containing (c) 0.9% sodium chloride solution, and (d) 5% dextrose solution. The reconstituted solutions were stored at room temperature for 6 and 24 hour intervals and also stored under refrigerated conditions (2° to 8° C.) for 45 hours. The tigecycline content present in the reconstituted solutions was then assayed. The percent of initial tigecycline content remaining in reconstituted formulations as obtained are given in Table 6.

TABLE 6

Percent of initial tigecycline content remaining in reconstituted formulations of
TYGACIL ® (tigecycline) [(Batch No. 30819) available from
Wyeth (India), manufactured in the UK; and
Composition in Example 1 at different time intervals Percent of Initial Tigecycline Content Remaining in Reconstituted Formulations

| Storage Time of the Reconstituted Formulation (Hr) | TYGACIL ® (tigecycline) (B. No 30819) available from Wyeth (India); manufactured in the UK | | | | Composition in Example 1 | | | |
| --- | --- | --- | --- | --- | --- | --- | --- | --- |
| | 5.3 mL 0.9% sodium chloride solution | 5.3 mL 5% dextrose solution | 5 mL reconstituted sodium chloride solution + 100 mL 0.9% sodium chloride | 5 mL reconstituted 5% dextrose solution + 100 mL 5% dextrose solution | 5.3 mL 0.9% sodium chloride solution | 5.3 mL 5% dextrose solution | 5 mL reconstituted sodium chloride solution + 100 mL 0.9% sodium chloride | 5 mL reconstituted 5% dextrose solution + 100 mL 5% dextrose solution |
| 0 (room temperature) | 100.00 | 100.00 | 100.00 | 100.00 | 100.00 | 100.00 | 100.00 | 100.00 |
| 6 (room temperature) | 86.32 | 86.44 | — | — | 98.35 | 98.19 | — | — |
| 24 (room temperature) | — | — | 80.13 | 85.68 | — | — | 94.65 | 93.91 |
| 45 (2 to 8° C.) | — | — | 94.81 | 95.93 | — | — | 97.29 | 95.36 |

We claim:

1. A stable parenteral formulation consisting of:
 (a) tigecycline;
 (b) an edetate;
 (c) lactose monohydrate;
 (d) sodium metabisulphite; and
 (d) water for injection,
 wherein the pH of the formulation prior to lyophilization is between 7.0 and 8.0.

2. The stable parenteral formulation of claim 1, consisting of:
 (a) 50 mg of tigecycline;
 (b) 1 mg of an edetate;
 (c) 100 mg of lactose monohydrate;
 (d) 0.05 mg of sodium metabisulphite; and
 (e) water.

3. The stable parenteral formulation of claim 1, wherein the edetate is disodium edetate.

4. The stable parenteral formulation of claim 1, wherein the tigecycline is present at 50 mg.

5. The stable parenteral formulation of claim 1, wherein the edetate is present at 1 mg.

6. The stable parenteral formulation of claim 1, wherein the lactose monohydrate is present at 100 mg.

7. The stable parenteral formulation of claim 1, wherein the sodium metabisulphite is present at 0.05 mg.

8. The stable parenteral formulation of claim 1, wherein the water is present in an amount sufficient to provide 1.5 ml for 50 mg of tigecycline.

9. The stable parenteral formulation according to claim 1 wherein the formulation does not degrade at least for 45 hours at 2° C. to 8° C.

10. The stable parenteral formulation according to claim 2 wherein the formulation does not degrade at least for 45 hours at 2° C. to 8° C.

* * * * *